(12) United States Patent
Hueffer et al.

(10) Patent No.: US 7,282,066 B2
(45) Date of Patent: Oct. 16, 2007

(54) PROCESSES FOR PREPARING AND USING TANNING AGENTS AND PRESERVATIVES

(75) Inventors: Stephan Hueffer, Ludwigshafen (DE); Guenter Scherr, Ludwigshafen (DE); Oliver Reese, Ludwigshafen am Rhein (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/543,605

(22) PCT Filed: Jan. 22, 2004

(86) PCT No.: PCT/EP2004/000491

§ 371 (c)(1),
(2), (4) Date: Jul. 28, 2005

(87) PCT Pub. No.: WO2004/067782

PCT Pub. Date: Aug. 12, 2004

(65) Prior Publication Data
US 2006/0053564 A1 Mar. 16, 2006

(30) Foreign Application Priority Data
Jan. 28, 2003 (DE) ................. 103 03 311
Nov. 20, 2003 (DE) ................. 103 54 396

(51) Int. Cl.
*C14C 3/00* (2006.01)
*C14C 9/00* (2006.01)

(52) U.S. Cl. .................... 8/94.19 R; 8/94.33
(58) Field of Classification Search .............. 8/94.1 R, 8/94.19 R, 94.33
See application file for complete search history.

(56) References Cited

U.S. PATENT DOCUMENTS

| | | | | |
|---|---|---|---|---|
| 2,546,018 A | | 3/1951 | Smith et al. | |
| 2,941,859 A | | 6/1960 | Filachione et al. | |
| 2,968,581 A | * | 1/1961 | Kress | 428/90 |
| 4,244,876 A | * | 1/1981 | Warner et al. | 252/182.12 |
| 4,448,977 A | * | 5/1984 | Warner et al. | 549/201 |
| 5,310,418 A | * | 5/1994 | Czech | 8/116.4 |
| 5,360,454 A | * | 11/1994 | Grief et al. | 8/94.33 |
| 6,033,442 A | * | 3/2000 | Denzinger et al. | 8/94.33 |
| 6,033,590 A | * | 3/2000 | Komforth et al. | 252/8.57 |
| 6,166,225 A | * | 12/2000 | Tanaka et al. | 549/347 |
| 6,559,346 B1 | * | 5/2003 | Therre et al. | 568/483 |

FOREIGN PATENT DOCUMENTS

| | | |
|---|---|---|
| DE | 38 11 267 | 5/1989 |
| DE | 44 44 709 | 6/1996 |
| EP | 0 066 224 | 12/1982 |
| EP | 0 459 168 | 12/1991 |
| EP | 0 970 148 | 1/2000 |
| WO | WO 01/16237 | * 3/2001 |

OTHER PUBLICATIONS

R. A. Burt et al.: "Vinyl ether hydrolysis. XIV. 2-Methoxy-2,3-dihydropyran: concurrent reation of vinyl ether and acetal functional groups", Canadian Journal of Chemistry, vol. 58, No. 21, pp. 2199-2202, Nov. 1, 1980. XP-002284867.
Ullmann's Encyclopedia of Industrial Chemistry, vol. A 15, pp. 259-281, 5$^{th}$ Edition, 1990.
Hans Herfeld: "Bibliothek des Leders", vol. II, p. 191, Umschau Verlag Frankfurt Am Main, 1988.
Vauk/Mueller: Grundoperationen chemischer Verfahrenstechnik, VCH Weinheim, 7$^{th}$ Edition, pp. 638-740 and 765-766, 1988.
U.S. Appl. No. 10/543,495, filed Jul. 27, 2005, Hueffer et al.
U.S. Appl. No. 10/543,605, filed Jul. 28, 2005, Hueffer et al.

* cited by examiner

*Primary Examiner*—Lorna M. Douyon
*Assistant Examiner*—Amina Khan
(74) *Attorney, Agent, or Firm*—Oblon, Spivak, McClelland, Maier & Neustadt, P.C.

(57) ABSTRACT

A process for the preparation of aqueous formulations, and aqueous formulations so prepared, the process comprising heating at least one cyclic compound of the formula I

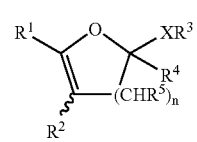

in the presence of water and of an acidic catalyst and, during or after the heating, $H-X-R^3$ is at least partially separated off, where, in formula I, X is selected from oxygen, sulfur and $N-R^6$, $R^1-R^6$ are as defined, and n is an integer from 1 to 4.

22 Claims, No Drawings

PROCESSES FOR PREPARING AND USING TANNING AGENTS AND PRESERVATIVES

The present invention relates to a process for the preparation of aqueous formulations, wherein at least one cyclic compound of the formula I

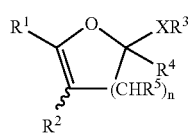

is heated in the presence of water and of an acidic catalyst and, during or after the heating, H—X—R$^3$ is separated off at least partially, where, in formula I, X is selected from oxygen, sulfur and N—R$^6$, R$^3$ and R$^6$ are identical or different and are selected from C$_1$-C$_{12}$-alkyl, C$_3$-C$_{12}$-cycloalkyl, substituted or unsubstituted, C$_7$-C$_{13}$-aralkyl, C$_6$-C$_{14}$-aryl, substituted or unsubstituted, formyl, CO—C$_1$-C$_{12}$-alkyl, CO—C$_3$-C$_{12}$-cycloalkyl, substituted or unsubstituted, CO—C$_7$C$_{13}$-aralkyl, CO—C$_6$-C$_{14}$-aryl, where, if X is N—R$^6$, R$^3$ and R$^6$ may be linked to one another with formation of a ring;

R$^1$, R$^2$ and R$^4$ are identical or different and are selected from hydrogen, C$_1$-C$_{12}$-alkyl, C$_3$-C$_{12}$-cycloalkyl, substituted or unsubstituted, C$_7$-C$_{13}$-aralkyl, C$_6$-C$_{14}$-aryl, substituted or unsubstituted, it being possible in each case for two neighboring radicals to be linked to one another with formation of a ring;

n is an integer from 1 to 4;

R$^5$ are identical or different and are selected from hydrogen, C$_1$-C$_{12}$-alkyl, C$_3$-C$_{12}$-cycloalkyl, substituted or unsubstituted, C$_7$-C$_{13}$-aralkyl, C$_6$-C$_{14}$-aryl, substituted or unsubstituted, it being possible for R$^5$ to be linked to R$^4$ or in each case two neighboring radicals R$^5$ to be linked to one another with formation of a ring.

The present invention furthermore relates to aqueous formulations prepared by the novel process, and the use of the novel aqueous formulations for the production of semifinished products or leather and of pulverulent formulations, which in turn can be used for the production of leather and as preservatives. Finally, the present invention relates to leather and semifinished products produced according to the invention.

Chrome tanning has been an important chemical treatment in leather production for more than 100 years, cf. for example *Ullmann's Encyclopedia of Industrial Chemistry*, Volume A15, pages 259 to 282 and in particular page 268 et seq., 5th Edition (1990), Verlag Chemie Weinheim. For ecological reasons, however, alternatives to chrome tanning are being sought.

Processes in which some or all of the chromium has been replaced by organic tanning agents are furthermore known. An example is the use of the so-called syntans, i.e. sulfonated condensates of formaldehyde and phenol or sulfonated naphthalene/formaldehyde condensates. A further example is the use of so-called vegetable tanning agents. However, both classes of tanning agents result in a high COD of the wastewaters and likewise give rise to reservations for environmental reasons. Moreover, it has been found that the lightfastness of the leathers is often unsatisfactory when sulfonated phenol/formaldehyde condensates are used (*Ullmann's Encyclopedia of Industrial Chemistry*, Volume A15, pages 259 to 282 and in particular page 270 et seq., 5th Edition (1990), Verlag Chemie Weinheim).

Furthermore, tanning with the use of aldehydes, in particular dialdehydes, for example glutardialdehyde, is known, cf., for example, H. Herfeld, Bibliothek des Leders, Volume III, page 191, Umschau Verlag Frankfurt/Main, 1984. A disadvantage is, however, that, with small amounts of glutardialdehyde, for example from 0.5 to 0.9% by weight, based on the pelt weight, the shrinkage temperatures are not above 70° C. and at that the semifinished products produced can therefore be dewatered only to an insufficient extent. During the shaving, glue formation occurs on the flesh side of the leather and adversely affects the quality of the leather.

In the literature, glutardialdehyde is often also referred to as glutaraldehyde, and both expressions are used in an equivalent way below.

When relatively large amounts of glutardialdehyde are used, work safety problems may arise owing to the toxic properties of the glutardialdehyde. Moreover, it is observed that completely tanned leather is generally obtained and that the subsequent variable processing, as desired in many tanneries, is no longer possible.

It is known that glutardialdehyde can be used in partly or completely acetalated form for tanning, for example as methylacetal (*Ullmann's Encyclopedia of Industrial Chemistry*, Volume A15, pages 259 to 282 and in particular page 273 et seq., 5th Edition (1990), Verlag Chemie Weinheim). However, the tanned semifinished products described generally tend to yellow rapidly.

DE-C 38 11 267 discloses that acetalation of glutardialdehyde or other dialdehydes which have 2 to 8 carbon atoms with short-chain alkylglycols, alkylpolyglycols, aliphatic alcohols, glycerol or saccharides has advantageous effects. However, the vapor pressure of the dialdehydes, which are readily formed again from the very hydrolysis-sensitive acetals, is still marked. Moreover, the performance characteristics of the leathers thus obtained can be further improved.

EP-A 0 066 224 discloses a process for the preparation of a precursor of glutardialdehyde. By heating 2-alkoxy-3,4-dihydropyrans with acid and water, a mixture of 2-hydroxy-6-alkoxytetrahydropyran, 2,6-dialkoxytetrahydropyran and glutardialdehyde is obtained, the amount of undesired oligomeric and polymeric byproducts forming being only small (page 2, line 33 et seq.). In the presence of water, the tetrahydropyran derivatives described liberate glutaraldehyde.

U.S. Pat. No. 2,546,018 discloses a process for the preparation of glutaraldehyde and C-substituted glutaraldehydes which is characterized with hydrolysis of glutaraldehyde in an aqueous, if appropriate aqueous acidic, medium. The glutaraldehyde and C-substituted dialdehydes obtainable by the process disclosed in U.S. Pat. No. 2,546,018 are purified by fractional distillation.

The same disadvantages with regard to tanning as those mentioned above are applicable to the glutaraldehyde or its derivatives obtainable according to EP-A 0 066 224, DE-A 44 44 709 and U.S. Pat. No. 2,546,018.

It is an object of the present invention to provide a process by means of which versatile aqueous formulations can be provided. It is a further object of the present invention to provide aqueous formulations which are suitable as versatile reagents for the production of semifinished products and of leather and which avoid the disadvantages known from the prior art. It is a further object of the present invention to provide aqueous formulations which are suitable as preservatives. Finally, it is an object of the present invention to provide uses for aqueous formulations.

We have found that these objects are achieved by the process defined at the outset. The novel process starts from compounds of the formula I

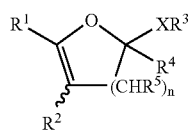

where the variables are defined as follows.

X is selected from oxygen, sulfur and N—$R^6$, oxygen being preferred.

$R^3$ and $R^6$ are identical or different and are selected from $C_1$-$C_{12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl, and n-dodecyl; preferably $C_1$-$C_6$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$-$C_4$-alkyl, such as methyl, ethyl, n-propyl, isopropyl, n-butyl, isobutyl, sec-butyl and tert-butyl, very particularly preferably methyl;

$C_3$-$C_{12}$-cycloalkyl, such as cyclopropyl, cyclobutyl, cyclopentyl, cyclohexyl, cycloheptyl, cyclooctyl, cyclononyl, cyclodecyl, cycloundecyl and cyclododecyl; cyclopentyl, cyclohexyl and cycloheptyl are preferred;

examples of substituted cycloalkyl groups are: 2-methylcyclopentyl, 3-methylcyclopentyl, cis-2,4-dimethylcyclopentyl, trans-2,4-dimethylcyclopentyl 2,2,4,4-tetramethylcyclopentyl, 2-methylcyclohexyl, 3-methylcyclohexyl, 4-methylcyclohexyl, cis-2,5-dimethylcyclohexyl, trans-2,5-dimethylcyclohexyl, 2,2,5,5-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,5,5-tetrachlorocyclohexyl, 2-thiomethylcyclopentyl, 2-thiomethylcyclohexyl, 3-thiomethyl-cyclopentyl and 3-thiomethylcyclohexyl;

$C_7$-$C_{13}$-aralkyl, preferably $C_7$- to $C_{12}$-phenylalkyl, such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$-$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably unsubstituted phenyl or substituted $C_6$-$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particuiarly preferably phenyl, substituted by one or more $C_1$-$C_{12}$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl and n-dodecyl; preferably $C_1$-$C_6$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl and sec-hexyl, particularly preferably $C_1$-$C_4$-alkyl, such as methyl, ethyl, n-propyl, isopropyl, n-butyl, isobutyl, sec-butyl and tert-butyl;

halogens, such as fluorine, chlorine, bromine and iodine, chlorine and bromine being preferred;

$C_1$-$C_{12}$-alkoxy groups, preferably $C_1$-$C_6$-alkoxy groups, such as methoxy, ethoxy, n-propoxy, isopropoxy, n-butoxy, isobutoxy, sec-butoxy, tert-butoxy, n-pentyloxy, isopentyloxy, n-hexyloxy and isohexyloxy, particularly preferably methoxy, ethoxy, n-propoxy and n-butoxy;

formyl,

CO—$C_1$-$C_{12}$-alkyl, such as acetyl, propionyl, n-butyryl, isobutyryl, sec-butyryl, tert-butyryl, n-valeroyl, isovaleroyl, sec-valeroyl, n-capryl, n-dodecanoyl; preferably CO—$C_1$-$C_4$-alkyl, such as acetyl, propionyl, n-butyryl, isobutyryl, sec-butyryl and tert-butyryl, very particularly preferably acetyl;

CO—$C_3$-$C_{12}$-cycloalkyl, such as cyclopropylcarbonyl, cyclobutylcarbonyl, cyclopentylcarbonyl, cyclohexylcarbonyl, cycloheptylcarbonyl, cyclooctylcarbonyl, cyclononylcarbonyl, cyclodecylcarbonyl, cycloundecylcarbonyl and cyclododecylcarbonyl; cyclopentylcarbonyl, cyclohexylcarbonyl and cycloheptylcarbonyl are preferred;

examples of substituted cycloalkyl groups are:

2-methylcyclopentylcarbonyl, 3-methylcyclopentylcarbonyl, 2-methylcyclohexyl-carbonyl, 3-methylcyclohexylcarbonyl, 4-methylcyclohexylcarbonyl, cis-2,5-dimethylcyclohexylcarbonyl, trans-2,5-dimethylcyclohexylcarbonyl, 2-methoxycyclopentylcarbonyl, 2-methoxycyclohexylcarbonyl, 3-methoxycyclopentylcarbonyl, 3-methoxycyclohexylcarbonyl, 2-chlorocyclopentylcarbonyl, 3-chlorocyclopentylcarbonyl, 2,4-dichlorocyclopentylcarbonyl, 2-chlorocyclohexyl-carbonyl, 3-chlorocyclohexylcarbonyl, 4-chlorocyclohexylcarbonyl, 2,5-dichlorocyclohexylcarbonyl, 2-thiomethylcyclopentylcarbonyl, 2-thiomethyl-cyclohexylcarbonyl, 3-thiomethylcyclopentylcarbonyl and 3-thiomethylcyclohexyl;

CO—$C_7$-$C_{13}$-aralkyl, preferably CO—$C_7$-$C_{12}$-phenylalkyl, such as phenylacetyl and ω-phenylpropionyl, particularly preferably phenylacetyl, CO—$C_6$-$C_{14}$-aryl, for example benzoyl, 1-naphthoyl, 2-naphthoyl, 1-anthroyl, 2-anthroyl, 9-anthroyl, 1-phenanthroyl, 2-phenanthroyl, 3-phenanthroyl, 4-phenanthroyl and 9-phenanthroyl, preferably benzoyl, 1-naphthoyl and 2-naphthoyl, particularly preferably benzoyl.

$R^1$, $R^2$ and $R^4$ are identical or different and are selected from hydrogen;

$C_1$-$C_{12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl, and n-dodecyl; preferably $C_1$-$C_6$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl and sec-hexyl, particularly preferably $C_1$-$C_4$-alkyl, such as methyl, ethyl, n-propyl, isopropyl, n-butyl, isobutyl, sec-butyl and tert-butyl, very particularly preferably methyl;

$C_3$-$C_{12}$-cycloalkyl, substituted or unsubstituted, such as cyclopropyl, cyclobutyl, cyclopentyl, cyclohexyl, cycloheptyl, cyclooctyl, cyclononyl, cyclodecyl, cycloundecyl and cyclododecyl; cyclopentyl, cyclohexyl and cycloheptyl are preferred;

examples of substituted cycloalkyl groups are: 2-methylcyclopentyl, 3-methylcyclopentyl, cis-2,4-dimethylcyclopentyl, trans-2,4-dimethylcyclopentyl 2,2,4,4-tetramethylcyclopentyl, 2-methylcyclohexyl, 3-methylcyclohexyl, 4-methylcyclohexyl, cis-2,5-dimethylcyclohexyl, trans-2,5-dimethylcyclohexyl, 2,2,5,5-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,5,5-tetrachlorocyclohexyl, 2-thiomethylcyclopentyl, 2-thiomethylcyclohexyl, 3-thiomethylcyclopentyl, 3-thiomethylcyclohexyl;

$C_7$-$C_{13}$-aralkyl, preferably $C_7$ to $C_{12}$-phenylalkyl, such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$-$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl; unsubstituted or substituted $C_6$-$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-Naphthyl, particularly preferably phenyl, unsubstituted or substituted by one or more $C_1$-$C_{12}$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl and n-dodecyl; preferably $C_1$-$C_6$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl and sec-hexyl, particularly preferably $C_1$-$C_4$-alkyl, such as methyl, ethyl, n-propyl, isopropyl, n-butyl, isobutyl, sec-butyl and tert-butyl;

halogens, such as fluorine, chlorine, bromine and iodine, chlorine and bromine being preferred;

$C_1$-$C_{12}$-alkoxy groups. preferably $C_1$-$C_6$-alkoxy groups, such as methoxy, ethoxy, n-propoxy, isopropoxy, n-butoxy, isobutoxy, sec-butoxy, tert-butoxy, n-pentyloxy, isopentyloxy, n-hexyloxy and isohexyloxy, particularly preferably methoxy, ethoxy, n-propoxy and n-butoxy;

it being possible in each case for two neighboring radicals to be linked to one another with formation of a ring. Thus, $R^1$ and $R^2$ together may be, for example, $C_1$-$C_8$-alkylene, unsubstituted or substituted by, for example, $C_1$-$C_{12}$-alkyl or $C_6$-$C_{14}$-aryl. Examples are: —$CH_2$—, —$CH(CH_3)$—, —$(CH_2)_2$—, —$CH_2$—$CH(CH_3)$—, —$CH_2$—$CH(C_2H_5)$—, —$(CH_2)_3$—, —$(CH_2)_2$—$CH(CH_3)$—, —$(CH_2)_2$—$CH(C_2H_5)$—, —$(CH_2)_2$—$CH(C_6H_5)$—, —$(CH_2)_4$—, —$(CH_2)_5$—, —$(CH_2)_6$—, —$(CH_2)_7$—, —$CH(CH_3)$—$CH_2$—$CH_2$—$CH(CH_3)$—, —$CH(CH_3)$—$CH_2$—$CH_2$—$CH_2$—$CH(CH_3)$—, preferably $C_3$-$C_5$-alkylene, such as —$(CH_2)_3$—, —$(CH_2)_4$— and —$(CH_2)_5$—.

n is an integer from 1 to 4, in particular 2 or 3;

$R^5$ are identical or different and are selected from hydrogen;

$C_1$-$C_{12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl, and n-dodecyl; preferably $C_1$-$C_6$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl and sec-hexyl, particularly preferably $C_1$-$C_4$-alkyl, such as methyl, ethyl, n-propyl, isopropyl, n-butyl, isobutyl, sec-butyl and tert-butyl, very particularly preferably methyl;

$C_3$-$C_{12}$-cycloalkyl, substituted or unsubstituted, such as cyclopropyl, cyclobutyl, cyclopentyl, cyclohexyl, cycloheptyl, cyclooctyl, cyclononyl, cyclodecyl, cycloundecyl and cyclododecyl; cyclopentyl, cyclohexyl and cycloheptyl are preferred;

examples of substituted cycloalkyl groups are: 2-methylcyclopentyl, 3-methyl-cyclopentyl, cis-2,4-dimethylcyclopentyl, trans-2,4-dimethylcyclopentyl 2,2,4,4-tetramethylcyclopentyl, 2-methylcyclohexyl, 3-methylcyclohexyl, 4-methyl-cyclohexyl, cis-2,5-dimethylcyclohexyl, trans-2,5-dimethylcyclohexyl, 2,2,5,5-tetramethylcyclohexyl, 2-methoxycyclopentyl, 2-methoxycyclohexyl, 3-methoxycyclopentyl, 3-methoxycyclohexyl, 2-chlorocyclopentyl, 3-chloro-cyclopentyl, 2,4-dichlorocyclopentyl, 2,2,4,4-tetrachlorocyclopentyl, 2-chloro-cyclohexyl, 3-chlorocyclohexyl, 4-chlorocyclohexyl, 2,5-dichlorocyclohexyl, 2,2,5,5-tetrachlorocyclohexyl, 2-thiomethylcyclopentyl, 2-thiomethylcyclohexyl, 3-thiomethyl-cyclopentyl and 3-thiomethylcyclohexyl;

$C_7$-$C_{13}$-aralkyl, preferably $C_7$- to $C_{12}$-phenylalkyl, such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$-$C_{14}$-aryl, substituted or unsubstituted, substituted and unsubstituted $C_6$-$C_{14}$-aryl radicals being defined as above.

In an embodiment of the present invention, $R^5$ may be linked to $R^2$ or $R^5$ to $R^4$ or $R^5$ to $R^3$ or, where n is greater than 1, in each case two neighboring radicals $R^5$ may be linked to one another with formation of a ring. Thus, $R^5$ and $R^2$ together may be, for example, $C_1$-$C_8$-alkylene, unsubstituted or substituted by $C_1$-$C_{12}$-alkyl or $C_6$-$C_{14}$-aryl. Examples are: —$CH_2$—, —$CH(CH_3)$—, —$(CH_2)_2$—, —$CH_2$—$CH(CH_3)$—, —$CH_2$—$CH(C_2H_5)$—, —$(CH_2)_3$—, —$(CH_2)_2$—$CH(CH_3)$—, —$(CH_2)_2$—$CH(C_2H_5)$—, —$(CH_2)_2$—$CH(C_6H_5)$—, —$(CH_2)_4$—, —$(CH_2)_5$—, —$(CH_2)_6$—, —$(CH_2)_7$—, —$CH(CH_3)$—$CH_2$—$CH_2$—$CH(CH_3)$—, —$CH(CH_3)$—$CH_2$—$CH_2$—$CH_2$—$CH(CH_3)$—, preferably $C_3$-$C_5$-alkylene, such as —$(CH_2)_3$—, —$(CH_2)_4$—, —$(CH_2)_5$—.

$R^2$ to $R^5$ are very particularly preferably each hydrogen. 2-Methoxy-2,3-dihydro-4H-pyran (formula I.1) is very particularly preferably selected as a compound of the formula I.

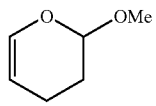

I.1

According to the invention, a cyclic compound of the formula I is heated in the presence of water. The amount of water may be chosen within wide ranges, and is preferably from 20 to 1 000, particularly preferably from 50 to 500, very particularly preferably from 60 to 200, % by volume, based on the cyclic compound of the formula I.

The novel process is carried out in the presence of an acidic catalyst which may consist of one or more acidic compounds.

Suitable acidic catalysts are, for example, phosphoric acid, in particular ortho-phosphoric acid, formic acid, acetic acid, acidic silica gels, acidic alumina, sulfuric acid, sulfonic acids, such as methanesulfonic acid or para-toluenesulfonic acid. Mixtures of, for example, sulfuric acid and phosphoric acid are also suitable. If nonaqueous solvents are employed, the use of $P_2O_5$ or a molecular sieve is conceivable. From 0.1 to 20% by weight, based on the cyclic compound of the formula I, of catalyst can be used. Of course, the catalyst or the catalysts can also be diluted, for example with water, before being used in the novel process.

In an embodiment of the present invention, the novel process is carried out at acidic pH, i.e. for example at a pH which is from 0 to 6.8, preferably from 0.1 to 4, particularly preferably from 0.5 to 4.

In an embodiment of the present invention, the novel process is carried out at from 40 to 120° C., in particular from 50 to 85° C.

The novel process can be carried out at any desired pressures from 0.1 to 100 bar, atmospheric pressure being preferred.

From 10 minutes to 24 hours, preferably from one to three hours are expedient as a time for the heating.

According to the invention, heating can be effected in the presence of an organic solvent or of a mixture of organic solvents, for example toluene, petroleum ether or n-heptane, but the addition of solvent is not necessary. If it is desired to use a solvent, an amount of from 10 to 100% by volume, based on the cyclic compound of the formula I, is suitable.

In a preferred embodiment of the present invention, the novel process is carried out without addition of ketone or monoaldehydes, examples of ketones are acetone, methyl ethyl ketone and methyl isobutyl ketone. Examples of monoaldehydes are acetaldehyde, benzaldehyde, crotonaldehyde and propionaldehyde.

During or after the heating, $H—X—R^3$ formed during the heating is separated off at least partially.

While the novel process is being carried out, $H—X—R^3$ is formed, in particular in an amount of up to one equivalent per cyclic compound of the formula I which is used.

In an embodiment of the present invention, $H—X—R^3$ is separated off during the heating, i.e. during the reaction, for example by distillation, the material stream separated off, which contains $H—X—R^3$ and may furthermore contain solvent, being admixed again only partially or not at all with the reaction mixture.

In another embodiment of the present invention, heating is first effected without separating off $H—X—R^3$, for example to reflux or to somewhat lower temperature than reflux, and separating off $H—X—R^3$ is begun after some time.

If $H—X—R^3$ is obtained in crystalline form, it can be separated off by filtration, preferably after the end of the reaction and cooling of the reaction mixture to, for example, room temperature.

In the context of the present invention, it is also possible first to effect heating without separating off $H—X—R^3$ and then to separate off $H—X—R^3$ at least partially by applying reduced pressure.

In the context of the present invention, separating off $H—X—R^3$ at least partially is to be understood as meaning that at least 30, preferably at least 85, particularly preferably at least 95, mol % of the $H—X—R^3$ formed during the novel process is separated off. $H—X—R^3$ can be separated off quantitatively, which is preferred particularly when $H—X—R^3$ has toxicologically unacceptable properties.

In a variant of the novel process, up to 99.5 mol % of the $H—X—R^3$ formed during the heating is separated off, and in a further variant up to 99.8 mol %.

On separating off $H—X—R^3$, water may also be partially separated off. In the present invention, however, quantitative separation of water is avoided.

The novel process gives aqueous formulations which are likewise a subject of the present invention and are also referred to below as novel aqueous formulations.

Before, during or after the novel, at least partial separation of $H—X—R^3$, the usually acidic novel aqueous formulations can be completely or partly neutralized. For example, basic alkali metal salts, such as alkali metal hydroxides, alkali metal carbonates and alkali metal bicarbonates, are suitable for the neutralization. Basic salts of sodium and potassium are particularly suitable. Basic salts of magnesium, for example magnesium oxide, are also suitable.

In some cases, the formation of a multiphase mixture is observed while carrying out the novel process. In said cases, it is possible to remove the respective aqueous phase by, for example, decanting or other methods known per se.

In a preferred embodiment of the present invention, a cyclic compound of the formula I is heated in the presence of at least one compound of the formula II

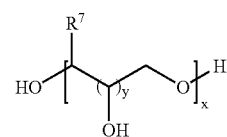

II where, in formula II, $R^7$ are different or preferably identical and are selected from $C_1$-$C_4$-alkyl, such as methyl, ethyl, n-propyl, isopropyl, n-butyl, isobutyl, sec-butyl and tert-butyl, very particularly preferably methyl, and in particular hydrogen.

x is an integer from 1 to 250, preferably from 3 to 50, particularly preferably from 5 to 20.

y is selected from zero and 1.

Examples of compounds of the formula II are ethylene glycol, propylene glycol, glycerol, diethylene glycol, dipropylene glycol, diglycerol ($R^7$=hydrogen, x=2, y=1), triethylene glycol, tetraethylene glycol and polyethylene glycols, for example polyethylene glycols having on average from 8 to 25 ethylene oxide units (number average), and furthermore mixed polyalkylene oxides which are obtainable, for example, by reacting mixtures of ethylene oxide and propylene oxide and, if appropriate, butylene oxide. Polyethylene glycol having on average from 7 to 12 ethylene oxide units (number average) and glycerol are particularly preferred.

If it is desired, according to the invention, to effect heating in the presence of at least one compound of the formula II, it is possible to choose from 3 to 300, preferably from 5 to 200, particularly preferably from 10 to 50%, by weight, based on the cyclic compound of the formula I, of a compound of the formula II.

The present invention furthermore relates to aqueous formulations obtainable by the novel process.

Novel aqueous formulations may have a water content of from 5 to 80, preferably from 20 to 50, % by weight. In the context of the present invention, the remainder of the novel formulations to 100% by weight is also referred to as active substance content of the novel formulations, and the reaction products resulting from the novel reaction described above, if appropriate as a mixture with unconverted cyclic compound of the formula I and, if appropriate, as a mixture with the compound of the formula II, are referred to as active substances.

Novel aqueous formulations may have a pH of from 2 to 9, preferably from 3 to 7, particularly preferably from 4 to 6.

For example, by means of mass spectrometry, it is possible to show that novel aqueous formulations contain only small amounts of dicarbonyl compound of the formula III

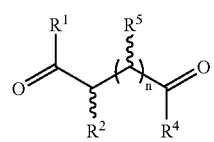

III for example up to 10% by weight, and substantially, for example, dimers, oligomers and polymers of dicarbonyl compound of the formula III which are formed by aldol condensation. The variables are as defined above.

The present invention furthermore relates to mixtures of dimers, oligomers and polymers of compound of the formula II, which may be contaminated by small amounts, for example up to 10% by weight, of compound of the formula III. Novel mixtures of dimers, oligomers and polymers can be obtained by the novel preparation process and subsequent isolation by methods known per se, for example removal, in particular evaporation, of water. Novel mixtures of dimers, oligomers and polymers of compound III may have a broad molecular weight distribution; thus, the average molecular weight $M_n$ may be from 100 to 100 000, preferably from 200 to 10 000, g/mol and the quotient $M_w/M_n$ may be from 2 to 20, preferably from 2.1 to 10.

Novel mixtures of dimers, oligomers and polymers of the compound of the formula III can be used without further processing or as an aqueous formulation for the production of semifinished products and of leather and as a preservative, in particular directly or as a pulverulent formulation.

The present invention furthermore relates to the use of the novel aqueous formulations for the production of semifinished products and of leather. The present invention furthermore relates to a process for the production of semifinished products or leather using at least one novel aqueous formulation.

In an embodiment of the present invention, novel aqueous formulations are used for the pretanning, tanning or retanning of animal hides.

The present invention furthermore relates to the use of novel aqueous formulations for the pretanning, tanning or retanning of animal hides and a process for the pretanning, tanning or retanning of animal hides using novel aqueous formulations.

The novel process for the pretanning, tanning or retanning of animal hides, (also referred to below as novel tanning process) starts from hides of animals, such as cattle, pigs, goats or deer, which have been pretreated by conventional methods. It is not important for the novel tanning process whether the animals were killed by slaughtering or died of natural causes. The conventional methods of pretreatment include, for example, liming, deliming, bating and pickling, and mechanical operations, for example for fleshing the hides.

The novel tanning process is usually carried out in the presence of water.

The novel tanning process is carried out, for example, by a procedure in which one or more novel aqueous formulations are added in one portion or in a plurality of portions immediately before or during the tanning step.

The novel tanning process is preferably carried out at a pH of from 2.5 to 4, it frequently being observed that the pH increases by about 0.3 to three units while the novel tanning process is being carried out. The pH can be increased by about 0.3 to three units by adding basifying agents.

The novel tanning process is carried out in general at from 10 to 45° C., preferably from 20 to 30° C. A duration of from 10 minutes to 12 hours, preferably from one to 3 hours, has proven useful. The novel tanning process can be carried out in any desired vessels customary in the tannery, for example by drumming in barrels or in rotatable drums having internals.

In a variant of the novel tanning process, one or more novel aqueous formulations are used together with one or more conventional tanning agents, for example with chrome tanning agents, mineral tanning agents, syntans, polymer tanning agents or vegetable tanning agents, as described, for example, in *Ullmann's Encyclopedia of Industrial Chemistry*, Volume A15, pages 259 to 282 and in particular page 268 et seq., 5th Edition (1990), Verlag Chemie Weinheim. The weight ratio of novel formulation to conventional tanning agents or the sum of conventional tanning agents is expediently from 0.01:1 to 100:1. In an advantageous variant of the novel process, only a few ppm of the conventional tanning agents are added to the novel formulations. However, it is particularly advantageous completely to dispense with the mixing of conventional tanning agents with novel formulations.

In a variant of the novel tanning process, one or more novel aqueous formulations are added in one portion or in a plurality of portions before or during the pretanning, in a particular variant as early as during pickling.

In a further variant of the novel tanning process, one or more novel aqueous formulations are added in one portion or in a plurality of portions before or during a retanning step. This variant is also referred to below as novel retanning process. The novel retanning process starts from pretanned hides, which are also referred to as semifinished products. These are treated with the novel aqueous formulations.

The novel retanning process can be carried out under otherwise conventional conditions. One or more, for example from 2 to 6, soaking steps are expediently chosen and washing with water can be effected between the soaking steps. The temperature during the individual soaking step is in each case from 5 to 60° C., preferably from 20 to 45° C. Further compositions usually used during the retanning, for example fatliquoring agents, leather dyes or emulsifiers, are expediently employed.

A further aspect of the present invention relates to semifinished products and leather produced by the novel tanning process. Novel leathers and novel semifinished products are produced using at least one novel aqueous formulation. Novel leathers and semifinished products have an overall advantageous quality, for example smooth grain, relatively homogeneous tanning over the cross section, improved tensile strength and body and less tendency to discoloration, in particular to yellowing.

In a special embodiment of the novel tanning process, novel formulations are used in the form of pulverulent formulations. The present invention therefore furthermore relates to the use of novel aqueous formulations for the preparation of pulverulent formulations and a process for the preparation of pulverulent formulations using novel aqueous formulations.

For the preparation of novel pulverulent formulations, for example, a procedure is adopted in which at least one novel aqueous formulation is dried, for example by evaporating the water and particularly preferably by spray-drying.

In a particular embodiment of the present invention, at least one novel aqueous formulation is mixed with one or more additives and then dried, for example by evaporating the water and in particular by spray-drying.

Suitable additives are as a rule solid particulate substances. They are preferably selected from starch, silica, for example in the form of silica gel, in particular in the form of spheroidal silica gels, sheet silicates, alumina and mixed oxides of silicon and aluminum.

In a special embodiment of the present invention, the following procedure is adopted: it has proven useful first to concentrate novel aqueous formulations to a residual water content of 50% by weight or less. Furthermore, if desired, one or more additives are added. The remaining volatile components are then removed. The resulting liquid, solid or oily concentrated formulations are preferably atomized in a spray dryer, preferably in a spray tower. Spray dryers are known to a person skilled in the art and are described, for example, in Vauck/Müller, *Grundoperationen chemischer Verfahrenstechnik*, VCH Weinheim, 1988, 7th Edition, pages 638-740 and pages 765-766, and in the literature cited therein.

The present invention furthermore relates to pulverulent formulations comprising from 10 to 100, preferably from 40 to 90, % by weight of active substance and from 0 to 90, preferably from 10 to 60, % by weight of one or more additives.

The novel pulverulent formulations may consist of fine particles having a mean particle diameter of from 100 nm to 0.1 mm. The particle diameters have a particle diameter distribution which may be narrow or broad. Bimodal particle size distributions are also conceivable. The particles themselves may have an irregular or spherical shape, spherical particle shapes being preferred. The novel pulverulent formulations can be metered under particularly hygienic conditions in the novel tanning process and are used instead of novel aqueous formulations.

It has furthermore been found that novel aqueous formulations and novel pulverulent formulations have a biocidal action.

A further aspect of the present invention relates to the use of the novel aqueous formulations and of the novel pulverulent formulations for preservation, and preservatives comprising novel pulverulent or aqueous formulations. The novel preservatives are suitable for the preservation of products, for example cosmetic products, and of surfaces.

The examples which follow illustrate the invention.

1. Preparation of the Novel Aqueous Formulations 1.1 to 1.3

The molecular weight determinations were carried out by gel permeation chromatography.

Stationary phase: Poly-(2-hydroxyethyl methacrylate) gel crosslinked with ethylene glycol dimethacrylate, commercially available as HEMA BIO from PSS, Mainz, Germany.

Mobile phase: Mixture of 30% by weight of tetrahydrofuran (THF), 10% by weight of acetonitrile, 60% by weight of 0.1 molar aqueous $NaNO_3$ solution Internal standard: 0.001% by weight of benzophenone Flow rate: 1.5 ml/min Concentration: 1% by weight in the mobile phase with internal standard Detection: UV/VIS at 254 nm Calibration with polystyrene sulfonate calibration unit from PPS.

1.1. Preparation of Aqueous Formulation 1.1

In a 2 liter three-necked flask having a condenser, stirrer and thermometer, 200 g of 2-methoxy-2,3-dihydro-4H-pyran (formula I.1; 2 mol), 30 g of polyethylene glycol having an average molecular weight $M_n$ of 400 g/mol, 200 ml of water and 6.5 g of a 50% by weight aqueous sulfuric acid were mixed and were heated to 77° C. for 3 hours. The pH was 1.

Thereafter, cooling to 35° C. was effected and the pH was then brought to 5 with 25% by weight of aqueous sodium hydroxide solution. Thereafter, heating to 56° C. was effected, stirring was carried out at 150 mbar for 3 hours and aqueous methanol was separated off.

400 g of novel aqueous formulation 1.1.

$M_n$: 580 g/mol, $M_w$: 1363 g/mol, $M_w/M_n$: 2.58

1.2. Preparation of Aqueous Formulation 1.2

In a 1 liter three-necked flask having a condenser, stirrer and thermometer, 300 g of 2-methoxy-2,3-dihydro-4H-pyran (formula I.1; 2.9 mol), 200 ml of water and 4.2 g of 50% by weight sulfuric acid were mixed and were heated to 80° C. for 1 hour. The pH was 1.

Thereafter, cooling to 35° C. was effected and the pH was then brought to 6 with 18 g of 10% by weight of aqueous sodium hydroxide solution. Thereafter, stirring was carried out at from 35 to 45° C. and from 80 to 100 mbar for 3 hours and aqueous methanol was separated off.

370 g of novel aqueous formulation 1.2 were obtained.

$M_n$: 326 g/mol, $M_w$: 660 g/mol, $M_w/M_n$: 2.02

1.3. Preparation of Aqueous Formulation 1.3

In a 1 liter three-necked flask having a condenser, stirrer and thermometer, 300 g of 2-methoxy-2,3-dihydro-4H-pyran (formula I.1; 2.9 mol), 200 ml of water and 6.7 g of 50% by weight sulfuric acid were mixed and were heated to 80° C. for 1 hour. The pH was kept at 0.5 during the reaction by adding further sulfuric acid. Thereafter, cooling to 30° C. was effected and the pH was brought to 6 with 33 g of 10% by weight of aqueous sodium hydroxide solution. Thereafter, stirring was carried out at 30° C. and from 60 to 70 mbar for 3 hours and aqueous methanol was separated off.

300 g of novel aqueous formulation 1.3 were obtained.

$M_n$: 400 g/mol, $M_w$: 455 g/mol, $M_w/M_n$: 2.39

2. Novel Tanning Experiments 2.1 to 2.3 and Comparative Experiment

Data in % by weight are based on the pickled weight, unless stated otherwise.

750 ml of water and 3% by weight, based on the pickled pelt, of a novel aqueous formulation according to examples 1.1. to 1.3. were added to strips, each weighing 2500 g, of a pickled cattle pelt having a split thickness of 2.5 mm, at a pH of 3.0-3.2 and 25° C., in a 10 l drum. After a drumming time of 60 minutes, 2% by weight of the sulfone tanning agent from EP-B 0 459 168, example K1, were added and drumming was effected for a further 2 hours. The pH was then brought to 4.9-5.1 with 0.5% by weight of magnesium oxide in the course of 6 hours. The liquor was discharged and the hide was washed with 300 ml of water. After samming, the hides were shaved to 1.6-1.8 mm. The novel semifinished products 2.1 to 2.3 were obtained.

The shave ability was determined by experiments on a shaving machine. The shaving machine operated with rotating blades. In the case of poor shave ability, the knives slid over the surface and the temperature on the surface of the leathers increased so that melting of a horny substance irreversibly damaged the hide. The rating was based on a rating system from 1 (very good) to 5 (poor).

Comparative experiment C 2.4 was carried out analogously, except that the novel adduct was replaced by 3% by weight of glutaraldehyde (50% by weight aqueous solution).

The shrinkage temperatures were determined by the method from DIN 53 336 (year 1977), the method having been modified as follows:

Point 4.1: The sample pieces had the dimensions 3 cm·1 cm; the thickness was not determined.

Point 4.2: Only one specimen instead of 2 specimens was tested per leather sample.

Point 6: Omitted

Point 7: The drying in a desiccator under reduced pressure was omitted.

Point 8: The shrinkage temperature was measured when the pointer moved back.

The rating of the shave ability and of the yellowing were effected according to the following rating system: 1 very good, 2 good, 3 satisfactory, 4 adequate.

TABLE 1

Result of tanning and analytical evaluation of the novel semifinished products

| Number | Semifinished product | Shaveability | Shrinkage temperature [° C.] | Yellowing |
|---|---|---|---|---|
| 2.1 | 2.1 | 3 | 76 | 1.5 |
| 2.2 | 2.2 | 2 | 77.5 | 2.5 |
| 2.3 | 2.3 | 2 | 79 | 2 |
| C 2.4 | Glutaraldehyde | 4 | 77 | 4 |

3. Production of Novel Leathers and Comparative Experiment

Data in % by weight are based on the shaved weight, unless stated otherwise.

3.1. Production of the Leather 3.1 from Semifinished Product 2.1

1800 g of semifinished product 2.1 were drummed together with the following agents for 20 minutes:

120% by weight of water, 5% by weight of the sulfone tanning agent from EP-B 0 459 168, example K1, and 4% by weight of a 30% by weight aqueous, partly NaOH-neutralized solution of a methacrylic acid homopolymer having the following analytical data: $M_n$ about 10 000;

Fikentscher K value: 12 (determined as a 1% by weight aqueous solution), viscosity of the 30% by weight solution: 65 mPa·s (DIN EN ISO 3219, 23° C.), pH 5.1.

6% by weight of the vegetable tanning agent Tara® (BASF Aktiengesellschaft) and 2% by weight of the resin tanning agent Relugan® S (BASF Aktiengesellschaft) and 2% by weight of an aqueous solution of dyes whose solids had the following composition:

70 parts by weight of dye from EP-B 0 970 148, example 2.18, 30 parts by weight of Acid Brown 75 (iron complex), Colour Index 1.7.16. were then metered and the mixture was drummed. After two hours, the pH was brought to 3.6 with formic acid. 6% by weight of a fatliquoring agent (cf. 4.) and 1% by weight of Lipamin OK® (BASF Aktiengesellschaft) were added as a fatliquoring component. After a drumming time of a further 60 minutes, the pH was brought to 3.2 with formic acid. Before the liquor was discharged, a sample of the liquor was taken. The liquor was discharged.

The leather thus obtained was washed twice with 100% by weight of water each time, stored moist overnight, sammed and then dried on a toggle frame at 50° C. Leather 3.1 was obtained. After staking, leather 3.1 was assessed as below.

The evaluation was carried out according to a rating system from 1 (very good) to 5 (poor). The evaluation of the liquor exhaustion was effected visually according to the criteria of residual dye (extinction) and turbidity (fatliquoring agent), from which the mean value was calculated.

EXAMPLES 3.2 TO 3.3, COMPARATIVE EXAMPLE C 3.4

The above example was repeated, but in each case with the novel semifinished products 2.2 to 2.3. For comparative example C3.4, the semifinished product from example C2.4 was further processed. The evaluation of the performance characteristics is shown in table 2.

TABLE 2

| Leather | Liquor exhaustion | Body | Grain tightness | Softness | Tensile strength [N] | Stitch tear resistance [N] | Levelness |
|---|---|---|---|---|---|---|---|
| 3.1 | 2 | 2.5 | 3 | 2.5 | 268 | 186 | 2.5 |
| 3.2 | 2.5 | 2.5 | 2 | 1.5 | 264 | 190 | 2 |
| 3.3 | 2 | 1.5 | 1.5 | 2 | 280 | 194 | 1.5 |
| C 3.4 | 3 | 3.5 | 3.5 | 3 | 247 | 191 | 3 |

The tensile strength was determined according to DIN 53328.

The stitch tear resistance was determined according to DIN 53331.

4. Preparation of the Fatliquoring Agent for Examples 2.1 to 2.3 and C2.4

The following were mixed in a 2 l kettle:

230 g of a polyisobutene having $M_n$=1000 g/mol and $M_w$=2000 g/mol 30 g of n-$C_{18}H_{37}O$—$(CH_2CH_2O)_{25}$—OH 5 g of n-$C_{18}H_{37}O$—$(CH_2CH_2O)_{80}$—OH 40 g of oleic acid 230 g of sulfited oxidized triolein The mixture was heated to 60° C. with stirring, and 470 g of water and 10 g of n—$C_{16}H_{33}O$—$(CH_2CH_2O)_7$—OH were added. The resulting emulsion was then passed through a gap homogenizer. A finely divided, stable emulsion was obtained.

We claim:

1. A process for the preparation of an aqueous formulation, comprising heating at least one cyclic compound of the formula I

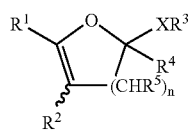

in the presence of at least one compound of the formula II

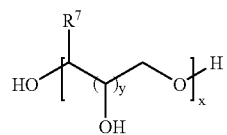

in the presence of water in an amount of 20 to 1000% by volume based on the cyclic compound of formula I, and of an acidic catalyst and, during or after the heating, H—X—$R^3$ is separated off at least partially, where, in formula I, X is selected from the group consisting of oxygen, sulfur and N—$R^6$, $R^3$ and $R^6$ are identical or different and are selected from the group consisting of $C_1$-$C_{12}$-alkyl, $C_3$-$C_{12}$-cycloalkyl, substituted or unsubstituted, $C_7$-$C_{13}$-aralkyl, $C_6$-$C_{14}$-aryl, substituted or unsubstituted, formyl, CO—$C_1$-$C_{12}$-alkyl, CO—$C_3$-$C_{12}$-cycloalkyl, substituted or unsubstituted, CO—$C_7$-$C_{13}$-aralkyl, CO—$C_6$-$C_{14}$-aryl, where, when X is N—$R_6$, $R_3$ and $R_6$ may be linked to one another with formation of a ring;

$R^1$, $R^2$ and $R^4$ are identical or different and are selected from the group consisting of hydrogen, $C_1$-$C_{12}$-alkyl, $C_3$-$C_{12}$-cycloalkyl, substituted or unsubstituted, $C_7$-$C_{13}$-aralkyl, $C_6$-$C_{14}$-aryl, substituted or unsubstituted, it being possible in each case for two neighboring radicals to be linked to one another with formation of a ring;

n is an integer from 1 to 4;

$R^5$ are identical or different and are selected from the group consisting of hydrogen, $C_1$-$C_{12}$-alkyl, $C_3$-$C_{12}$-cycloalkyl, substituted or unsubstituted, $C_7$-$C_{13}$-aralkyl, $C_6$-$C_{14}$-aryl, substituted or unsubstituted, it being possible for $R^5$ to be linked to $R^4$ or in each case two neighboring radicals $R^5$ to be linked to one another with formation of a ring;

$R^7$ are identical or different and are selected from the group consisting of hydrogen and $C_1$-$C_4$-alkyl, x is an integer from 1 to 250 and y is selected from the group consisting of zero and 1.

2. The process according to claim 1, wherein it is carried out without addition of ketone or monoaldehyde.

3. The process according to claim 1, wherein X is oxygen.

4. The process according to claim 1, wherein $R^1$, $R^2$, $R^4$ and $R^5$ are each hydrogen.

5. The process according to claim 1, wherein n is 2.

6. A process for the production of semifinished products or leather comprising the process according to claim 1 and further comprising treating semifinished products or leather with the aqueous formulation.

7. A process for the preparation of a pulverulent formulation comprising the process according to claim 1 and further comprising drying an aqueous formulation.

8. The process according to claim 7, wherein the aqueous formulation and one or more additives are mixed with one another and then dried.

9. The process according to claim 8, wherein the one or more additives are selected from the group consisting of starch, silica, sheet silicates, alumina and mixed oxides of silicon and aluminum.

10. A process for the preparation of a pulverulent formulation according to claim 8, wherein the pulverulent formulation is obtained by spray-drying.

11. A process comprising preserving a product by incorporating the pulverulent formulation according to claim 7 in said product.

12. The process according to claim 1, wherein the at least one cyclic compound comprises 2-methoxy-2,3-dihydro-4H-pyran.

13. The process according to claim 1, wherein the at least one compound of the formula II is polyethylene glycol having on average from 7 to 12 ethylene oxide units or glycerol.

14. The process according to claim 12, wherein the at least one compound of the formula II is polyethylene glycol having on average from 7 to 12 ethylene oxide units or glycerol.

15. The process according to claim 1, wherein the at least one compound of the formula II is present in an amount of 10 to 50% by weight based on the weight of the at least one cyclic compound.

16. The process according to claim 1, wherein the formulation comprises at least one of dimers, oligomers and polymers of a dicarbonyl compound of the formula III which are formed by aldol condensation, and up to 10% by weight of said dicarbonyl compound of the formula III:

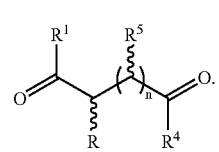

17. The process according to claim 1, wherein the water is present in an amount of 60 to 200% by volume, based on the cyclic compound of the formula I.

18. The process according to claim 1, wherein said H—X—$R^3$ is separated off at least partially by distillation.

19. The process according to claim 1, wherein said H—X—$R^3$ is separated off at least partially by filtration.

20. The process according to claim 1, wherein said H—X—$R^3$ is separated off at least partially by applying reduced pressure.

21. The process according to claim 1, wherein at least 85 mol % of said H—X—R3 formed is separated off.

22. The process according to claim 1, wherein at least 95 mol % of said H—X—$R^3$ formed is separated off.

* * * * *